US006502264B1

(12) United States Patent
Clothier et al.

(10) Patent No.: US 6,502,264 B1
(45) Date of Patent: Jan. 7, 2003

(54) ARTICULATED BED WITH A VIBRATION AWAKENING SYSTEM

(75) Inventors: Donald Ralph Clothier, Rockford, IL (US); Adam Michael Weinman, Tampa, FL (US)

(73) Assignee: Steven J. Antinori, Tampa, FL (US)

( * ) Notice: Subject to any disclaimer, the term of this patent is extended or adjusted under 35 U.S.C. 154(b) by 29 days.

(21) Appl. No.: 09/657,006

(22) Filed: Sep. 7, 2000

(51) Int. Cl.[7] .......................... A61H 1/00; G04B 47/00; A61G 7/015

(52) U.S. Cl. ................................ 5/915; 368/12; 601/57

(58) Field of Search ............................ 5/616, 618, 915, 5/916, 666, 674; 601/46, 48, 49, 56, 57; 368/12

(56) References Cited

U.S. PATENT DOCUMENTS 804,653 A * 11/1905 Garris ......................... 601/24
900,293 A * 10/1908 Metz ......................... 5/915 X
924,127 A * 6/1909 Arms ........................ 5/915 X
2,323,081 A * 6/1943 Baird ......................... 318/128
2,396,947 A * 3/1946 Gutteridge .................. 368/252
2,448,162 A * 8/1948 Wettlaufer ................... 601/26
2,460,133 A * 1/1949 La Pedus ................... 5/915 X
2,561,481 A * 7/1951 Rody ........................ 5/915 X
2,580,598 A * 1/1952 Rody ........................ 5/915 X
2,719,769 A * 10/1955 Murphy ......................... 5/618
2,923,122 A * 2/1960 Inman ......................... 368/12
3,955,222 A * 5/1976 Pater ......................... 5/915 X
4,028,882 A * 6/1977 Muncheryan ................ 368/12
4,093,944 A * 6/1978 Muncheryan ............... 340/521
4,180,810 A * 12/1979 Muncheryan .......... 340/384.71
4,232,661 A * 11/1980 Christensen ................. 601/48
4,370,602 A * 1/1983 Jones, Jr. et al. ........... 5/674 X
4,371,815 A * 2/1983 Jones, Jr. et al. ............. 318/14
RE31,603 E 6/1984 Christensen
4,535,760 A * 8/1985 Ikeda et al. ................... 601/57
4,544,867 A * 10/1985 Jones, Jr. et al. ........... 318/129
4,639,959 A * 2/1987 Roca ............................. 5/674
4,667,358 A * 5/1987 Penterman ..................... 5/674
5,022,384 A * 6/1991 Freels et al. .................. 601/57
5,076,260 A * 12/1991 Komatsu ..................... 601/59
5,144,600 A * 9/1992 Cheng ......................... 368/12
5,235,258 A * 8/1993 Schuerch ..................... 318/16
5,475,883 A * 12/1995 Martin .......................... 5/674
5,544,376 A 8/1996 Fromson
5,600,214 A * 2/1997 Fromson .................... 5/915 X
5,686,884 A * 11/1997 Larkin et al. ............... 340/506
5,787,528 A 8/1998 Antinori
6,077,238 A * 6/2000 Chung ......................... 601/57
6,236,621 B1 * 5/2001 Schettino ..................... 368/10

* cited by examiner

*Primary Examiner*—Robert G. Santos
(74) *Attorney, Agent, or Firm*—Diller, Ramik & Wight

(57) ABSTRACT

An articulated bed includes head/back and foot/leg sections each provided with a conventional electrically powered motor driver for driving an associated massage/ vibrator motor. A remote control handset includes a microprocessor for generating time-of-day signals and a key pad is used to encode a bed code which is bed-specific and a wake time. The microcontroller compares a predetermined wake-time setting with present time of day and generates a wake authorization signal which is transmitted to a receiver associated with the bed. The received signal of the receiver is conducted to a microcontroller which authenticates the bed code signal and responsive thereto energizes one or both of the vibrators at the desired wake time, preferably initiating minimum vibrations and progressively increasing vibrations to a maximum to wake an individual in/upon the bed. The microcontroller of the receiver includes circuitry to automatically cut off the vibrator motor(s) after a predetermined length of vibration time, such as thirty (30) minutes, to assure vibration termination absent human intervention.

10 Claims, 1 Drawing Sheet

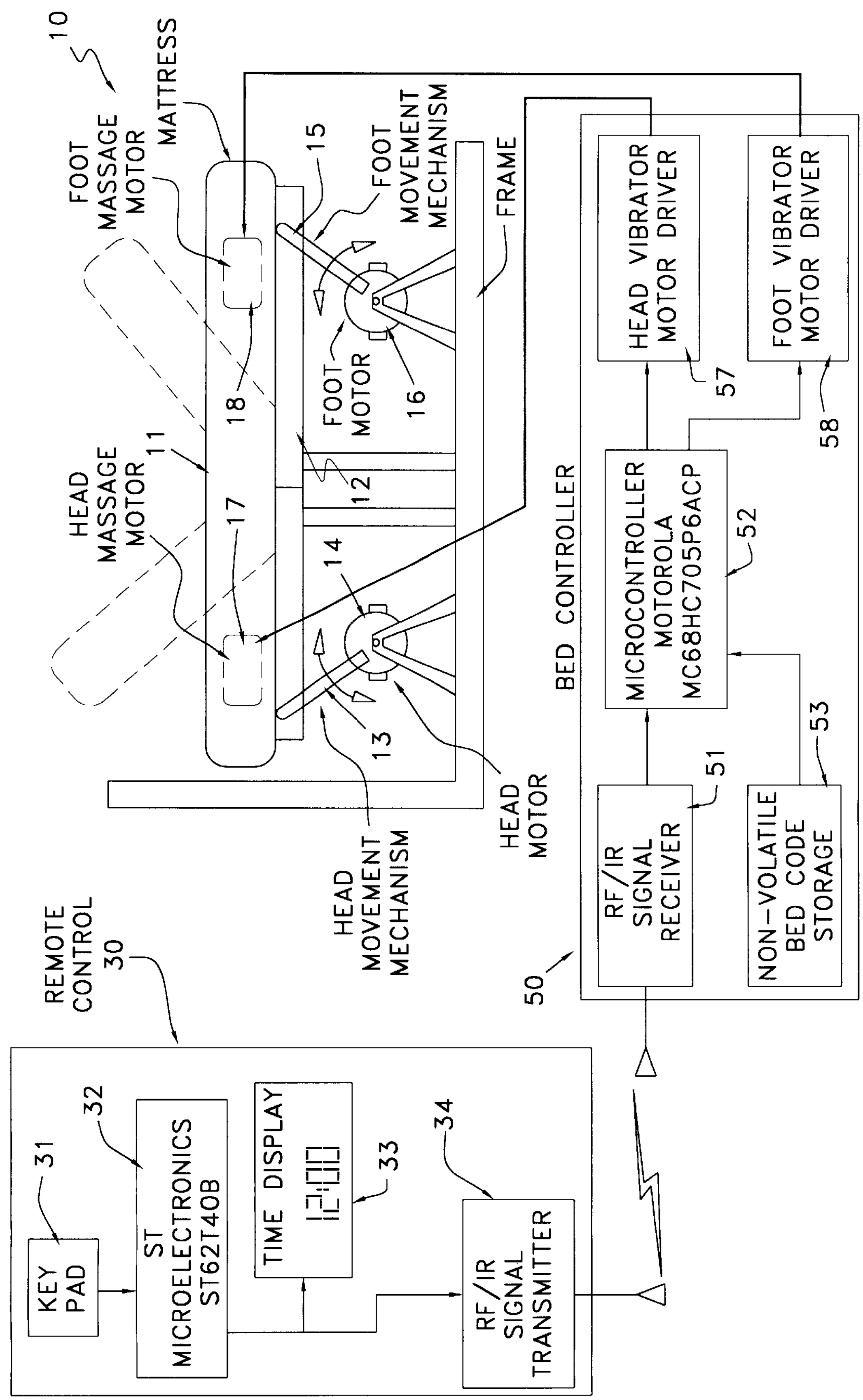
10
MATTRESS
FOOT MASSAGE MOTOR
HEAD MASSAGE MOTOR
11
17
18
15
FOOT MOVEMENT MECHANISM
FOOT MOTOR
16
12
14
13
HEAD MOVEMENT MECHANISM
HEAD MOTOR
FRAME
BED CONTROLLER
HEAD VIBRATOR MOTOR DRIVER
57
FOOT VIBRATOR MOTOR DRIVER
58
MICROCONTROLLER MOTOROLA MC68HC705P6ACP
52
RF/IR SIGNAL RECEIVER
51
NON-VOLATILE BED CODE STORAGE
53
50
REMOTE CONTROL 30
KEY PAD
31
ST MICROELECTRONICS ST62T40B
32
TIME DISPLAY
33
RF/IR SIGNAL TRANSMITTER
34

ARTICULATED BED WITH A VIBRATION AWAKENING SYSTEM

BACKGROUND OF THE INVENTION

The present invention relates to an articulated bed which includes head/back and foot/leg sections individually articulated by associated motors and linkages with one or both sections also including a vibrator or massage motor. Such articulated or adjustable beds are relatively conventional, along with hand-held controllers associated therewith. Examples of such articulated beds can be found in U.S. Pat. Nos. 5,787,528, Re. 31,603 and 5,544,376 granted Aug. 4, 1998, Jun. 19, 1984 and Aug. 13, 1996, respectively.

Heretofore no articulated beds have been provided with a vibrating mechanism for the purpose of awakening a person/patient lying on or upon such bed. The desirability of being gently awakened by vibrations, as opposed to the cataclysmic sounds of an electric alarm buzzer or the blare of a radio broadcasting raucous sound or song are readily apparent. Vibration is both emotionally and physiologically therapeutic to the human mind and body, and awakening to vibrations is similarly therapeutic, particularly when awakening occurs, as in keeping with the present invention, at relatively low vibrations which progressively increase to a maximum thereby awakening a person slowly, gently and absent day-beginning anxiety, as most often occurs when one awakens to a conventional alarm clock or radio alarm.

SUMMARY OF THE INVENTION

In keeping with the foregoing, it is a primary object of the present invention to provide a novel system by which a bed can be vibrated at a predetermined time to awake a person sleeping thereon. The vibration awakening system of the present invention utilizes one or both of conventional massage or vibrator motors associated with the head and foot sections of a conventional articulated bed. However, rather than utilizing these vibrator motors strictly for conventional therapeutic/massage purposes while a person is awake, the present invention permits a desired wake-time to be programmed into a microprocessor/microcontroller which in turn continuously compares the present time of day with the stored wake-time setting. When a match occurs between the latter times, the microprocessor generates a wake authorization signal which through a transmitter is transmitted to a receiver associated with the articulated bed. Another conventional microprocessor/microcontroller energizes the vibrator motor or motors in response to the wake authorization signal awakening the user by vibrations which last a predetermined length of time.

In further accordance with this invention, the amplitude or speed of vibration is preferably progressively increased from inception to a maximum such that a person is gently and progressively awakened.

In further accordance with the invention, the vibrating motors are deactivated after a predetermined length of time, such as thirty (30) minutes, to assure termination of vibration operation absent human intervention.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWING

The drawing is a diagrammatic block diagram of a conventional articulated bed, and illustrates a remote control for encoding both a bed code and a wake-time code into a microprocessor which through a transmitter transmits bed code and wake-time code signals to a remote receiver associated with the bed and another microprocessor for energizing either or both vibrator motors associated with the head and foot sections of the bed.

DETAILED DESCRIPTION OF THE DRAWING

An articulated or adjustable bed is illustrated in the drawing and is generally designated by the reference numeral 10. The adjustable bed 10 is entirely conventional and the specifics thereof, including head and foot section drive motors, head and foot section massage motors, control circuitry; a wireless remote control encoder and transmitter and associated circuitry; a receiver and associated control circuitry, etc. can be found in U.S. Pat. No. 5,787,528, and the latter is incorporated hereat by reference.

The articulated bed 10 includes a mattress 11 resting atop an articulated or adjustable frame 12 which can be moved between the solid and phantom outline positions shown in the drawings by a conventional head moving mechanism 13 powered by a head motor 14 and a conventional foot moving mechanism 15 powered by a foot motor 16 under the control of a bed controller/bed controller circuit 50 which is in turn responsive to a wireless remote control or handset 30. A conventional head massage vibrating motor 17 and a conventional foot massage vibrating motor 18 are located at respective head and foot ends (unnumbered) of the mattress or support 11 and/or the frame 12, and each of the vibration motors 17, 18 can be energized in the manner more specifically described in U.S. Pat. Nos. 5,544,376 and Re. 31,603 which are also incorporated herein by reference.

The wireless hand-held remote control or controller 30 includes a conventional key pad 31 by which a user can manually encode a bed-specific bed code signal and a predetermined wake time setting into conventional means, such as a conventional microprocessor or microcontroller 32 (ST 62T40B). The microcontroller 32 includes circuitry which generates a periodic signal which along with embedded code creates a time-of-day function, and this time can be displayed by a conventional liquid crystal (LC) display 33. The microcontroller 32 includes embedded programming means for continuously comparing the wake-time setting stored therein by the key pad 31 with the present time of day and upon achieving a match, the microcontroller 32 generates a wake authorization signal which is transmitted by a conventional transmitter 34 to a conventional receiver 51 of the bed control system 50 which is housed conventionally upon the frame 12 of the bed 10.

The micro-controller 32 can also control the transmitter or transmitting means 14 for transmitting at least two substantially immediately consecutive wake authorization signals to assure reception thereof by the receiving means 51 of the bed control system Both the bed-specific bed code signal and the wake authorization signal are conducted to a microcontroller 52 and upon a match, the microcontroller 52 generates signals turning on a head vibrator motor driver 57 of the head vibrator motor 17 and a foot vibrator motor driver 58 of the foot vibrator motor 18, whereby one or both begin vibrating substantially at the predetermined wake time encoded into the remote controller 30 by the user. Vibrations created by either or both of the vibrator motors 17, 18 awake a person asleep upon the mattress 11.

Preferably, the microcontroller 52 controls the speed of the vibrator drivers 57, 58, respectively, from initial very low speed to progressively higher speeds until a maximum speed is reached which correspondingly progressively increases the vibrations afforded by the massage motors 17, 18 from low amplitudes/ speeds to maximum higher amplitudes/speeds. The result achieved thereby is that of quietly and gently awakening a sleeping person through progressively increasing vibrations.

The microcontroller 52 also includes conventional circuitry and embedded code for timing-out the drive of the head and foot vibrator motor drivers 57, 58 approximately thirty (30) minutes after initial energization thereof to assure vibration termination absent human intervention.

Although a preferred embodiment of the invention has been specifically illustrated and described herein, it is to be understood that minor variations may be made in the apparatus without departing from the spirit and scope of the invention, as defined the appended claims.

We claim:

1. A vibration awakening system comprising a bed upon which rests a mattress, means for vibrating said mattress, means remote of said bed for establishing a predetermined wake-time setting, means remote from said bed for maintaining time of day, means for continuously comparing the predetermined wake-time setting with the present time-of-day and generating a wake authorization signal upon achieving a match between the latter times, means for transmitting the wake authorization signal, receiving means associated with said bed for receiving said wake authorization signal, means responsive to said wake authorization signal for energizing said vibrating means at a wake-time corresponding substantially to said predetermined wake-time setting, said wake authorization signal responsive means progressively and automatically increases only the speed of the vibrations of a single signal generated by said vibrating means, and means for controlling the transmitting means for transmitting at least two substantially immediately consecutive wake authorization signals to assure reception thereof by said receiving means.

2. The vibration awakening system as defined in claim 1 wherein said wake authorization signal responsive means automatically deactivates said vibrating means after a predetermined vibration time length.

3. The vibration awakening system as defined in claim 1 including means for automatically disabling said energizing means after a predetermined time period of operation of said vibrating means whereby vibration generation terminates absent human intervention.

4. The vibrating awakening system as defined in claim 1 wherein said bed includes relatively movable back and leg bed sections, and said vibrating means is associated with at least one of said back and leg bed sections.

5. The vibrating awakening system as defined in claim 1 wherein said bed includes relatively movable back and leg bed sections, and said vibrating means is associated with both of said back and leg sections.

6. The vibrating awakening system as defined in claim 1 wherein said wake authorization signal responsive means is a microcontroller.

7. The vibrating awakening system as defined in claim 1 wherein said comparing and generating means is a microcontroller.

8. A vibration awakening system comprising a bed upon which rests a mattress, means for vibrating said mattress, means remote of said bed for establishing a predetermined wake-time setting, means remote from said bed for maintaining time of day, means for continuously comparing the predetermined wake-time setting with the present time-of-day and generating a wake authorization signal upon achieving a match between the latter times, means for transmitting the wake authorization signal, receiving means associated with said bed for receiving said wake authorization signal, means responsive to said wake authorization signal for energizing said vibrating means at a wake-time corresponding substantially to said predetermined wake-time setting, said wake authorization signal responsive means progressively and automatically increases only the speed of the vibrations of a single signal generated by said vibrating means, means remote from said bed for generating a bed code signal indicative of a specific bed, said transmitting means being further operative for transmitting said bed code signal, said receiving means including means responsive to a specific bed code signal for effecting energization of said vibrating means, and means for controlling the transmitting means for transmitting at least two substantially immediately consecutive wake authorization signals to assure reception thereof by said receiving means.

9. The vibration awakening system as defined in claim 8 wherein said wake authorization signal responsive means automatically deactivates said vibrating means after a predetermined vibration time length.

10. The vibration awakening system as defined in claim 8 including means for automatically disabling said energizing means after a predetermined time period of operation of said vibrating means whereby vibration generation terminates absent human intervention.

* * * * *